United States Patent [19]

Gutkowski et al.

[11] Patent Number: 4,660,763

[45] Date of Patent: Apr. 28, 1987

[54] VAPOR-DISPENSING DEVICE

[75] Inventors: Ronald R. Gutkowski; Edward J. Martens, both of Racine County, Wis.

[73] Assignee: S. C. Johnson & Son, Inc., Racine, Wis.

[21] Appl. No.: 774,686

[22] Filed: Sep. 11, 1985

[51] Int. Cl.$^4$ .............................................. A61L 9/12
[52] U.S. Cl. ...................................... 239/43; 239/56; 239/121
[58] Field of Search ...................... 239/34, 37, 39, 42, 239/43, 51, 51.5, 53, 55-59, 120, 121, 328; 98/40.2, 114, 121.1

[56] References Cited

U.S. PATENT DOCUMENTS

| | | |
|---|---|---|
| 344,640 | 6/1886 | Dobbs .................... 98/114 |
| 1,725,071 | 8/1929 | Gaby . |
| 1,952,707 | 3/1934 | Germonprez ............. 98/114 |
| 2,126,525 | 8/1938 | Anderson ................ 98/121.1 |
| 2,955,525 | 10/1960 | Steffner .............. 98/40.2 X |
| 3,096,705 | 7/1963 | Goettl .................. 98/121.1 |
| 3,137,631 | 6/1964 | Soloway . |
| 3,218,263 | 11/1965 | Boyle . |
| 3,310,235 | 3/1967 | Zbinden . |
| 3,511,436 | 5/1970 | Kessler . |
| 3,532,536 | 10/1970 | Noyes et al. . |
| 3,637,428 | 1/1972 | Aleckner, Jr. . |
| 3,655,129 | 4/1972 | Seiner ................. 239/34 X |
| 3,685,734 | 8/1972 | Paciorek et al. ........... 239/56 |
| 3,697,311 | 10/1972 | Aleckner, Jr. . |
| 3,713,965 | 1/1973 | Widiger et al. . |
| 3,767,787 | 10/1973 | Segal . |
| 3,768,725 | 10/1973 | Pilaro . |
| 3,775,227 | 11/1973 | Wilbert et al. . |
| 3,817,821 | 6/1974 | Gallini . |
| 3,900,635 | 8/1975 | Funderburk, Jr. et al. . |
| 3,903,335 | 9/1975 | Jones . |
| 3,932,693 | 1/1976 | Shaw et al. . |
| 3,994,439 | 11/1976 | Van Breen et al. . |
| 4,011,172 | 3/1977 | Marsan et al. . |
| 4,064,296 | 12/1977 | Bornstein et al. . |
| 4,127,688 | 11/1978 | Bieler et al. . |
| 4,145,001 | 3/1979 | Weyenberg et al. ........ 239/56 |
| 4,161,284 | 7/1979 | Rattan .................. 239/56 X |
| 4,178,401 | 12/1979 | Weinberg et al. . |
| 4,196,065 | 4/1980 | Gaussens et al. . |
| 4,206,844 | 6/1980 | Thukamoto et al. . |
| 4,224,367 | 9/1980 | Scholle . |
| 4,225,373 | 9/1980 | Bieler et al. . |
| 4,247,584 | 1/1981 | Widiger et al. . |
| 4,252,846 | 2/1981 | Romesberg et al. . |
| 4,318,763 | 3/1982 | Bieler et al. . |
| 4,322,465 | 3/1982 | Webster . |
| 4,348,438 | 9/1982 | Canterino . |
| 4,352,844 | 10/1982 | Bornstein . |
| 4,352,849 | 10/1982 | Mueller . |
| 4,367,816 | 1/1983 | Wilkes . |
| 4,410,582 | 10/1983 | Tsunashima et al. . |
| 4,428,892 | 1/1984 | Berliner . |
| 4,502,630 | 3/1985 | Haworth et al. ........... 239/34 |
| 4,558,820 | 12/1985 | Harris, Jr. .............. 239/57 X |

FOREIGN PATENT DOCUMENTS 492749  2/1976  Australia ................ 98/40.2

Primary Examiner—Joseph F. Peters, Jr.
Assistant Examiner—Mary Beth O. Jones

[57] ABSTRACT

A device for dispensing air-treating vapors having a frame, two relatively movable support members comprising the frame having facing, substantially parallel support surfaces and being relatively movable to adjust the spacing between the surfaces, and a flexible, generally flat dispensing pouch sandwiched between the support surfaces. The dispensing pouch, which will have a burstable inner storage container of flowable air-treating composition, will be of a size to extend beyond the outer border of grill units of the two support members with peripheral portions of the support members being in the form of reservoirs for any of the air-treating composition which may flow out of the periphery of the pouch beyond the outer border of the grill units.

16 Claims, 6 Drawing Figures

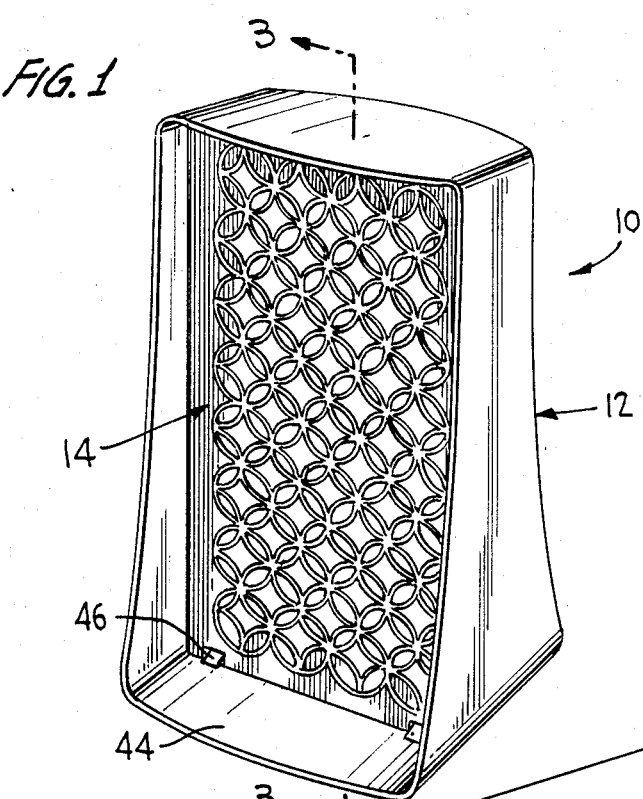
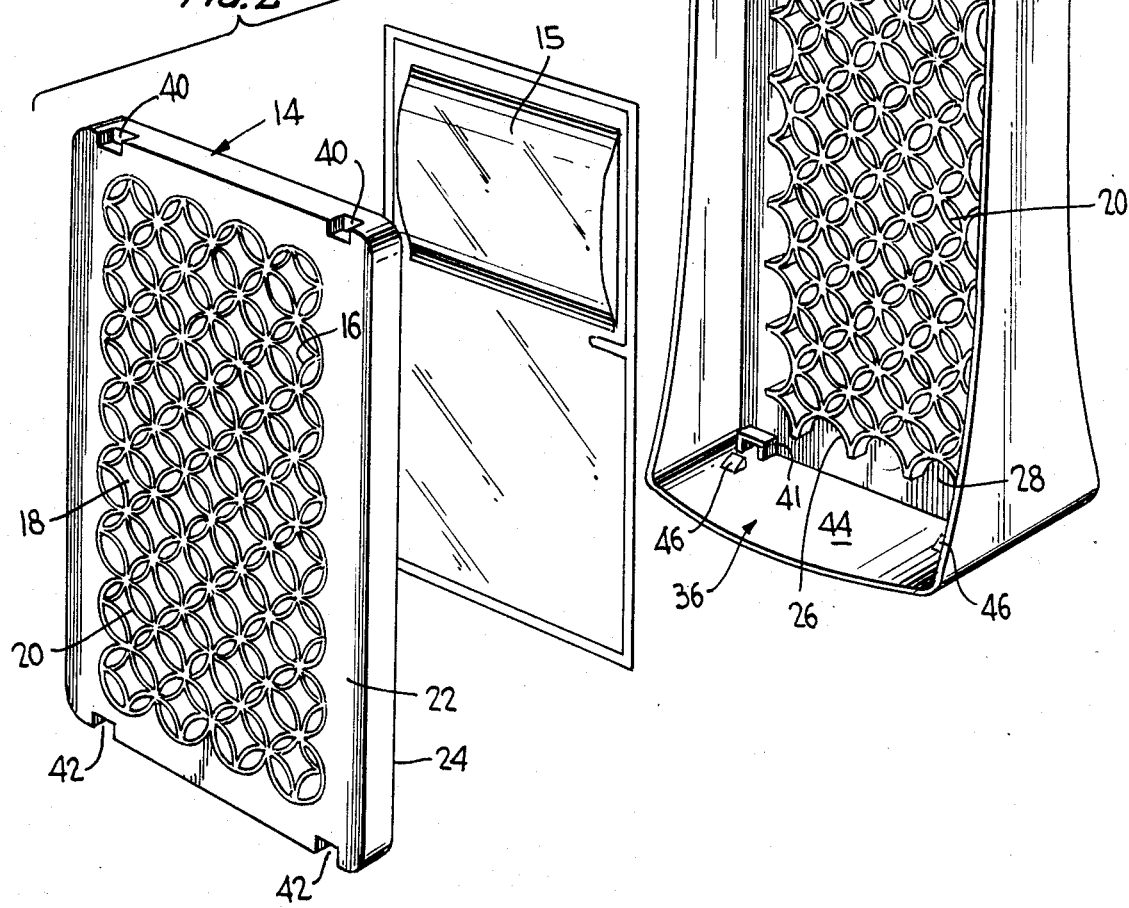

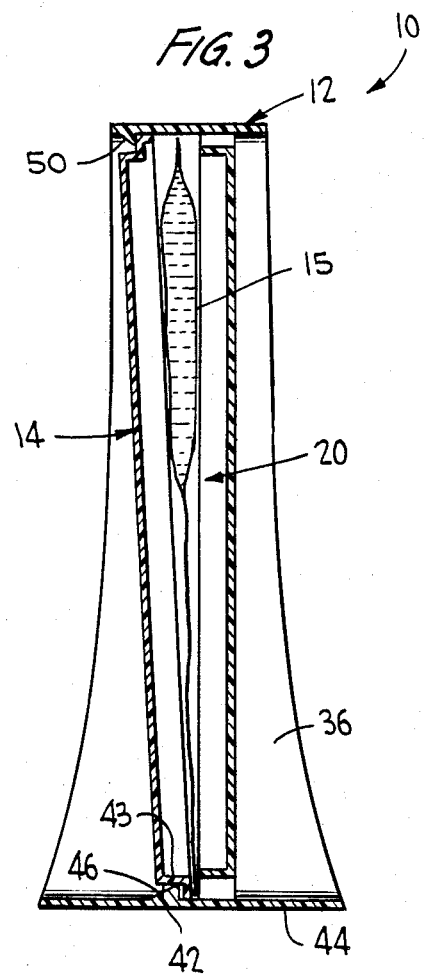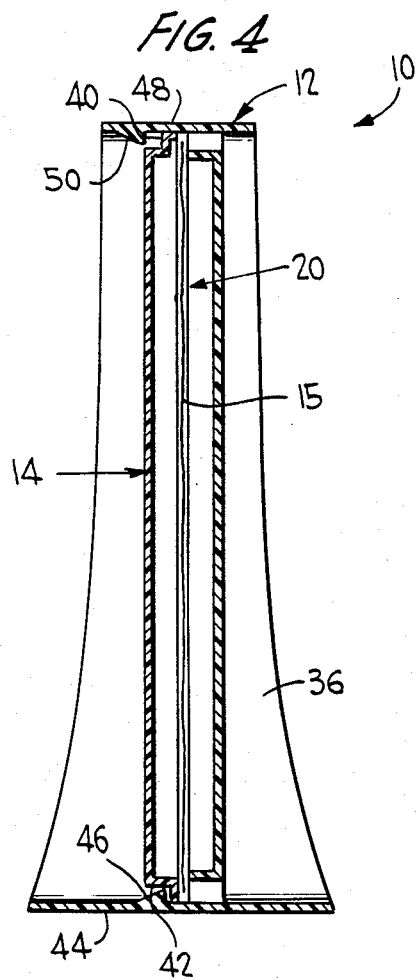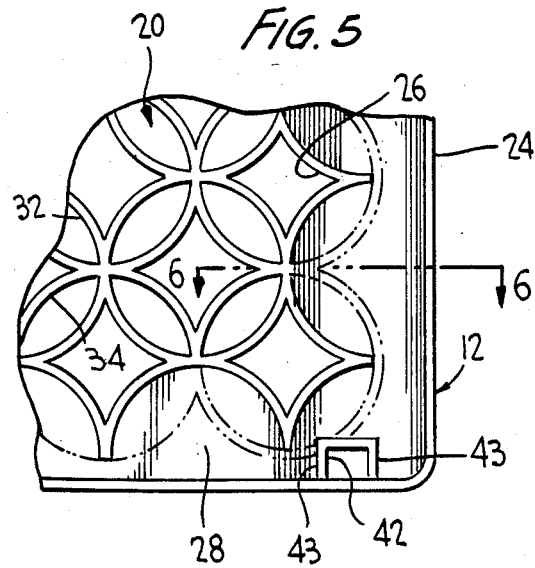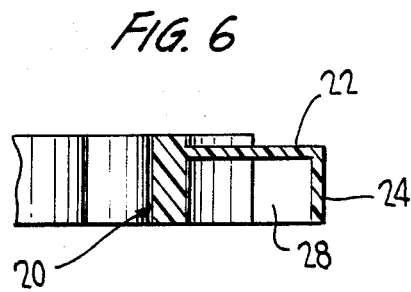

4,660,763

VAPOR-DISPENSING DEVICE

FIELD OF INVENTION

This invention relates to devices for providing a continuous release of air-treating vapors. More specifically, this invention relates to devices for releasing vapors to the atmosphere at a substantially constant rate.

BACKGROUND OF THE INVENTION

Commonly assigned co-pending U.S. Pat. No. 4,558,820 discloses a device for dispensing air-treating vapors from a flexible, generally flat dispenser pouch containing a liquid air-treating composition. That device includes a frame or housing which may be adapted to rest on a table top or other surface, or to be hung or otherwise supported. Two support members are mounted across the frame such that a flexible, generally flat dispensing pouch can be supported between them. The two support members are movable relative to one another so that the flexible pouch, which is sandwiched between these support surfaces of the support members can be squeezed by sandwiching force exerted through the support members.

The flexible dispenser pouch includes an inner storage container filled with a flowable, vaporizable air-treating composition, preferably a liquid. Such inner storage container is burstable by sandwiching pressure exerted through these support surfaces to release the air-treating composition into a dispenser pouch for dispensing by permeation of vapor to the surface of the pouch and into the atmosphere.

Although the device described in 4,558,820 is highly useful, it has been found that in that device the pouch is subject to possible leakage about its periphery when the inner storage container is ruptured.

DESCRIPTION OF THE INVENTION

The present invention relates to the provision of a reservoir in a vapor-dispensing device for receiving any air-treating composition which may escape from the periphery of the pouch containing the same.

To this end, there has been provided support members in the form of grill assemblies, one integral with the housing and one separate and apart but telescoped within the housing of the device, which is so constructed as to have a peripheral storage area in part defined by the outer border of a grill unit and in part by a facing panel and a peripheral flange.

OBJECTS OF THE INVENTION

It is an object of this invention to provide grill assemblies for a device for dispensing air-treating vapors overcoming problems of the prior art.

Another object of this invention is to provide an improved air-treating vapor dispenser of the type including a liquid air-treating composition within a flexible enclosure, the dispenser having a built-in reservoir area for receiving any escaping liquid composition from the periphery of the flexible enclosure.

These primary and other important objects of the invention will be apparent from the following description of a preferred embodiment of the invention and from the accompanying drawings.

BRIEF DESCRIPTION OF THE DRAWINGS

In the drawing,

FIG. 1 is a perspective view of the device and shows the general details thereof;

FIG. 2 is a exploded perspective view showing the various components of the device;

FIG. 3 is a vertical sectional view taken generally along the line 3—3 of FIG. 1 and shows the device before bursting of the inner storage container;

FIG. 4 is another sectional view similar to FIG. 3, but showing the grill assemblies moved together to effect bursting of the inner storage container;

FIG. 5 is an enlarged fragmentary elevation of one corner of the movable grill assembly viewed from the backside and shows the details of the storage reservoir formed therein; and FIG. 6 is an enlarged fragmentary vertical sectional view taken generally along the line 6—6 of FIG. 5 and shows further the details of the reservoir.

Referring now to the drawings in detail, it will be seen that there is illustrated in FIG. 1 a vapor-dispensing device 10 formed in accordance with this invention.

As is best shown in FIG. 2, the vapor-dispensing device 10 includes two similar grill assemblies 12, 14. The grill assembly 12 will have positioned therein a flexible, generally flat vapor-dispensing pouch generally identified by the numeral 15, the pouch 15 being sandwiched between supporting surfaces of the two grill assemblies 12 and 14 when they are assembled as is shown in FIG. 3.

The grill assembly 14 has an outer peripheral surface 16 defining a central opening 18 which has positioned therein a grill unit generally identified by the numeral 20.

The surface 16 is bordered by a generally planar facing panel 22 which has extending from one face thereof along the outer periphery thereof a peripheral flange 24. A border 26 of the grill unit 20, as is best shown in FIG. 5, is sealed along the inner periphery of the facing panel 22, with the inner periphery of the facing panel 22 corresponding generally to the outline of the grill outer border 26.

Further, as is best shown in FIGS. 5 and 6, the projecting grill border 26 and the projecting peripheral flange 24 which project generally the same distances from the facing panel 22 and, in conjunction with the facing panel 22, define a reservoir 28. Although the FIGS. 5 and 6 depict only one grill unit assembly, it will be understood by reference to the drawings that it is necessary for two grill units to be in mating engagement in order to form the reservoir. The drawings depict only one grill unit so that the space between the grill units can be easily discerned.

In the illustrated embodiment of the grill unit 20, the grill unit is of a molded construction integral with the surface 16 and being formed by two sets 32, 34 of cylinders and part cylinders. The cylinders of each of the sets are arranged in touching rows and columns of a generally rectangular pattern. The cylinders of the two sets 32, 34 are offset relative to one another so that each complete cylinder of one set has disposed therein four quadrants of portions of four cylinders of the other set.

If desired, for ornamental purposes, the grill unit 20 may extend beyond the opposite face of the facing panel 22 as is shown in FIG. 6. As is shown in FIG. 5 in phantom lines, the grill pattern may overlap the facing panel 22.

Although in the grill assembly 14 the peripheral flange 24 extends only from one face of the facing panel 22, in the grill assembly 12 the peripheral flange is in the form of a housing which extends a considerable distance beyond the facing panel 22 formed integral therewith with the facing panel 22 being offset from the edge of the housing 12 or 14 depending upon the panel being examined. It is to be understood that the housing 36 of grill assembly 12 is slightly larger than the outer periphery of the grill assembly 14 so that the grill assembly 14 may be telescoped therein and frictionally retained in position within the housing 36.

With particular reference to FIGS. 2 and 5, it will be seen that along the upper edge thereof adjacent to two upper corners, the grill assembly 14 is provided with notches 40. Similar notches 42 are formed along the lower edge of the grill assembly 14. Each of these notches is backed up by an internal projection 43 formed on the inner surface of the facing panel 22 and the peripheral flange 24 as is shown in FIG. 5.

The housing 36 has a bottom wall 44, and projecting upwardly from that bottom wall is a pair of tapered retaining lugs 46. The lugs 46 are intended to be received in the notches 42. Rearward of lugs 46 are boxes 41 (only one being illustrated in FIG. 2) which accept grill 22 and in the area of indents 42 and with the inside of grill 22 complete the seal.

Also, as is shown in FIG. 2, the housing 36 includes a top wall 48 which has depending therefrom lugs 50 which are similar to the lugs 46 and which are receivable in the notches 40.

As shown, the bottom wall 44 and top wall 48 have a slight curvature. Accordingly, when placed on furniture only a small part of the surface is in contact with the furniture, preventing marking of the furniture by trapped product vapors.

With reference to FIGS. 3 and 4, it will be seen that the device 10 is assembled by placing the pouch 15 within the housing 36 generally against the face of the grill unit 20 of the grill assembly 12. Then the grill assembly 14 is entered into the housing 36 and snapped over the lugs 46, with the lugs 46 entering into the notches 42. At this time the pouch 15 is in an unsqueezed, unruptured condition.

When it is desired to utilize the device, it is necessary to rupture the bag or bags within the pouch 15. To accomplish this, the grill assembly 14 is advanced towards the grill unit 20 of the grill assembly 12, rupturing the bags within the pouch 15. The grill assembly 14 is snapped over the lugs 50 during initial assembly, and the lugs function as retainers for the grill assembly 14. The lugs 50 enter into the notches 40 to retain the pouch 15 clamped between the grill units 20. It is to be understood that the periphery of the pouch 15 will extend beyond the border 26 of the two grill units, and the periphery edges of the pouch 15 will overlap the reservoir 28 for receiving any of the liquid which may flow out of the peripheral portions of the pouch 15.

At this time, it is pointed out that the grill assemblies 12, 14 may be formed of plastic material such as high-density polyethlyene, polypropylene, nylons, or any of a variety of suitable materials.

As will be apparent, the burstable pouch which is utilized in accordance with the present invention can be of the type described in U.S. Pat. No. 4,558,820 and more particularly as disclosed in commonly assigned U.S. Pat. No. 4,539,793. Further, the material within the pouch to be dispensed can be any vapor-emitting material such as a perfume. It has been found, however, that vapor-emitting substances such as a perfume which have been thickened are particularly desirable. Thus, perfume compositions thickened with fumed silica marketed under the tradename Cabosil by Cabot Corporation, Boston, Mass., are particularly desirable. These thickened perfume compositions are known in the art.

While in the foregoing specification, this invention has been described in relation to only a single preferred embodiment of the invention and many details have been set forth for the purpose of illustration, it will be apparent to those skilled in the art that the invention is susceptible to additional embodiments and that certain of the details described herein can be varied considerably without departing from the basic principles of the invention.

It is claimed:

1. A grill assembly device for dispensing air treating vapors, said grill assembly comprising:
   (a) at least 2 grill assemblies, at least one of which is comprised of an outer frame including a generally planar facing panel, a peripheral flange extending from one face of the outer periphery of said facing panel, said grill unit also extending from said one face, and said grill unit having an outer border sealingly connected to said facing panel in spaced relation to said peripheral flange;
   whereby said grill unit outer border, said peripheral flange and said facing panel and a portion of said other grill assembly combine to define a reservoir for receiving vaporizable air-treating composition when in mating engagement with said other grill assembly.

2. A grill assembly according to claim 1 wherein said facing panel has an inner border corresponding to said grill unit outer border.

3. A grill assembly according to claim 1 wherein said facing panel has an inner border corresponding to said grill unit outer border, said facing panel inner border being generally of a scalloped configuration.

4. A grill assembly according to claim 1 wherein said grill assembly is of a one-piece molded construction.

5. A grill assembly according to claim 1 wherein said grill unit also projects from an opposite face of said facing panel.

6. A grill assembly according to claim 5 wherein said peripheral flange projects from only said one face.

7. A grill assembly according to claim 1 wherein said peripheral flange projects from only said one face.

8. A grill assembly according to claim 1 wherein said peripheral flange and said grill unit project substantially the same distance from said facing panel.

9. A grill assembly according to claim 1 wherein said peripheral flange extends beyond said grill unit and defines a housing for receiving said other grill assembly in opposed relation, the other grill assembly being slightly smaller.

10. A grill assembly according to claim 1 wherein said grill unit is defined by two sets of cylinders with each set being formed of cylinders in a touch rectangular pattern, and said two sets being diagonally offset from one another.

11. A device for dispensing air-treating vapors, said device comprising a pair of grill assemblies, each of said grill assemblies including an outer frame defining a central opening and a grill unit in said opening, said outer frame including a generally planar facing panel, a peripheral flange extending from one face of the outer periphery of said facing panel generally normal to the plane of said facing panel, said grill unit also extending from said one face, and said grill unit having an outer border sealingly connected to said facing panel in spaced relation to said peripheral flange; said grill unit outer border, said peripheral flange and said facing panel combining to define a reservoir for receiving vaporizable air-treating compositions, said peripheral flange of one of said grill assemblies being in the form of a housing, receiving the other of said grill assemblies, a vapor-dispensing pouch sandwiched between said grill units and having peripheral edges overlapping said reservoirs, and said reservoirs being in facing generally sealing relation around the periphery of said pouch.

12. A device according to claim 11 wherein said housing and said outer frame of said other grill assembly having cooperating locking means for retaining said grill units in assembled relation.

13. A device according to claim 11 wherein each of said facing panels has an inner border corresponding to a respective grill unit outer border.

14. A device according to claim 11 wherein each of said grill assembly is of a one-piece molded construction.

15. A device according to claim 11 wherein said housing extends from opposite faces of said facing panel of said one grill assembly, and said peripheral flange of said other grill assembly extends from one face only.

16. A device according to claim 11 wherein said peripheral flange and said grill unit of said one grill assembly project substantially the same distance from said facing panel thereof.

* * * * *